United States Patent
Ando et al.

(10) Patent No.: US 6,521,272 B1
(45) Date of Patent: Feb. 18, 2003

(54) SUGAR SUPER-TOLERANT YEAST FOR CONFECTIONERY AND BAKERY

(75) Inventors: Masayasu Ando, Tokyo (JP); Natuko Nakamura, Saitama-ken (JP); Yoshiaki Shinomiya, Tokyo (JP)

(73) Assignee: Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 09/523,093

(22) Filed: Mar. 10, 2000

(30) Foreign Application Priority Data

Mar. 12, 1999 (JP) .......................................... 11-067565
Mar. 31, 1999 (JP) .......................................... 11-092673

(51) Int. Cl.$^7$ ................................................ C12N 1/18
(52) U.S. Cl. ...................... 426/62; 435/7.31; 435/255.2
(58) Field of Search ........................... 435/255.1, 255.2, 435/34, 7.31; 426/62, 19, 27, 249, 656

(56) References Cited

U.S. PATENT DOCUMENTS 5,801,049 A    9/1998    Endo

FOREIGN PATENT DOCUMENTS

EP    0 921 190    6/1999

OTHER PUBLICATIONS

Tanaka et al. "Screening of Sugar–Tolerant Baker's Yeast for Sweet Buns", *Nippon Shokuhin Kogyo Gakkaishi*, vol. 31, No. 10, pp. 661–664, Oct. 1984.

*Primary Examiner*—Keith Hendricks
(74) *Attorney, Agent, or Firm*—Browdy and Neimark

(57) ABSTRACT

The invention provides (1) yeasts with high leavening ability enough for bakery in an ultra-high sugar range and with high sugar tolerance (osmotic pressure tolerance), and (2) yeasts with high leavening ability enough for bakery in an ultra-high sugar range and with high sugar tolerance (osmotic pressure tolerance) and high freezing tolerance which characteristically exert sufficient leavening ability of dough blended with sugar above 40 parts by weight per 100 parts by weight of flour, to enable the production of high-quality bread items including white bread in a low sugar range to sweet roll items or fermented confectioneries in a high sugar range, irrespective of the bakery process.

5 Claims, No Drawings

SUGAR SUPER-TOLERANT YEAST FOR CONFECTIONERY AND BAKERY

FIELD OF THE INVENTION

The present invention relates to novel yeasts and the use thereof.

DESCRIPTION OF THE RELATED ART

Bread is grouped in a wide variety of items, including French bread with no sugar added, white bread having a low sugar range, which is prepared by adding sugar in an amount of 5 to 6% to flour, croissants and butter rolls having a medium sugar range, which are prepared by adding sugar in an amount of 8 to 15% to flour, Danish pastry and confectionery bread having a high sugar range, which are prepared by adding sugar in an amount of 20 to 30% to flour, fermented confectioneries, such as beam-jam sweet, and coffee cake and brioche, which are prepared by adding sugar in an amount of 35 to 50% to flour. Furthermore, bakery processes can be divided into scratch process (including straight bakery process and intermediate seed bakery process) and frozen dough processes. Therefore, these processes and bread items are used in such a wide variety of combinations.

For producing the bread items in the low sugar range to the high sugar range, conventionally, various yeasts with various fermentative abilities have been used in such a complicated manner that yeast with high freezing tolerance should be used for the frozen dough process. However, no yeast with sugar tolerance enough for fermentation of dough items [for bean-jam sweet roll, fermented confectioneries, etc.] in a blend of sugar at a content as high as 35% or more to flour has yet been present. Accordingly, many bakers have managed to treat such dough items by prolonging the duration of the fermentation more than necessary or raising the quantity of yeast, to prepare the products. Nevertheless, these products are currently of no bread quality primarily intended and have poor bulky appearance.

Problems that the Invention is to Solve

It is an object of the invention to provide yeasts with high sugar tolerance (or osmotic pressure tolerance) having high excellent fermentative abilities in a super-high sugar range, so as to solve the problems. In current circumstances where sweet bread and confectioneries with high sugar contents are desired in general, more specifically, the invention has been attained for the purpose of providing novel yeasts with super-high.sugar tolerance, which conventionally have never existed and are hardly affected (of which the fermentative abilities are hardly reduced) by the osmotic pressure of high contents of fat or fatty oil or egg blended in dough at a super-high sugar content of 30 to 40% or more. Conventional yeasts under the influence of osmotic pressure can never yield bread products of excellent quality from dough in a blend of fat or fatty oil or egg at a super-high sugar content of 30 to 40% or more. Owing to the progress in bakery technology and the diversification of bread items in recent years, yeast should be selected and used, depending on the intended bread item. Thus, many types of yeast are essentially needed. In terms of laborious works in the use of a different yeast each time, which is not practical industrially, novel yeasts with excellent properties are provided, from the respect that one yeast concurrently having these properties can satisfy the whole aspect.

In other words, the invention provides excellent yeasts with great specificity from the respect of super-high sugar tolerance. Additionally, the invention can firstly provide new useful yeasts satisfying all the needs, which has never been obtained conventionally and which does not require the proper use of yeasts having different properties, depending on the intended products.

Means for Solving the Problems

The invention relates to yeasts which high sugar tolerance (or osmotic pressure tolerance). Specific characteristic properties of the inventive yeasts are as described below.

1. The yeasts have a leavening ability of dough blended with sugar in an amount of 5 to 25% to flour for bread loaf and confectionery bread (in the low to high sugar range), at the same level as that of routine general types of yeast (for example, Regular Yeast manufactured by Oriental Yeast Co., Ltd), by the straight dough method and the sponge dough method, to produce bread of large volume and stable quality.

2. The yeasts have sugar tolerance (osmotic pressure tolerance) capable of fermenting dough at a very high sugar concentration, such as dough containing sugar in an amount of 30 to 50% to flour.

Of course, the present yeasts may be used to make variants breads and sweet rolls by using dough containing other sugar in place of sucrose; examples of said other sugar are glucose, fructose, liquid inverted sugar, etc.

Various methods can be adopted so as to obtain the inventive yeasts. By the mating method, for example, the intended strain can be obtained highly efficiently. Firstly, therefore, strains with high fermentative abilities and with a character of increased sugar tolerance are selected from among bakers' yeast strains. The individual yeast strains are inoculated on a spore forming culture medium in a conventional manner to form the spores; after the examination of the properties of the resulting spores, then, strains with the same bakery performance as general practical yeasts for bread making and also with a high leavening ability of 40%-sugar blended dough are satisfactorily screened from among strains grown by the traditional mating method. It is needless to say that the intended strains may be created by a mutation process. As the mutation process, routine methods can be adopted widely, including physical processes with γ ray, ultraviolet ray and temperature difference, etc. and processes with mutagens such as ethidium bromide, nitrogen mustard, diepoxybiitane, colchicine, peroxide, and purine derivatives.

One of the new yeast strains thus obtained was designated *Saccharomyces cerevisiae* P-712 and deposited under FERM BP-7034 at National Institute of Bioscience and Human—Technology Agency of Industrial Science and Technology. The bacteriological properties are described below.

Bacteriological Properties of the Strain P-712

1. Growth state

Good growth in YM liquid culture medium.

Cell morphology: spherical to egg shape; 3 to 7×4 to 8 $\mu$.

MM agar culture medium: good growth; colony (white, glossy, and smooth).

2. Ascospore

Formed in potassium acetate culture medium; ascospore of spherical shape.

3. Individual physiological properties 3-1. Optimum growth conditions: temperature of 28 to 32° C.; pH 4.5 to 6.5.

3-2. Growth range: temperature of 5 to 40° C.; pH 2.5 to 8.0.

3-3. Assimilation of nitrate salt: none.
3-4. Fat decomposition: none.
3-5. Carotenoid generation: none.
3-6. Prominent organic acid generation: none.
3-7. Vitamin requirement: biotin and pantothenic acid.
3-8. Sugar tolerance: sufficient leavening ability can be exerted in dough blended with sucrose above 30 to 40 parts by weight or more to 100 parts by weight of flour.
4. Fermentability and assimilability of carbon source

|  | Fermentability | Assimilability |
|---|---|---|
| D-Glucose | + | + |
| D-Galactose | + | + |
| Maltose | + | + |
| Sucrose | + | + |

In accordance with the present invention, furthermore, new yeast strains are provided, having a high leavening ability in a super-high range as well as freezing tolerance.

Various methods can be adopted so as to obtain the inventive yeasts. By the mating method, for example, the intended strain can be obtained highly efficiently. Firstly, therefore, strains with high fermentative abilities and with a character raising both freezing tolerance and sugar tolerance are selected from among bakers' yeast strains. The individual yeast strains are inoculated on a spore forming culture medium in a conventional manner to form the spores; after the examination of the properties of the resulting spores, then, strains with the same bakery performance as general practical yeasts for bread making and also with a high leavening ability of 40%-sugar blended dough and freezing tolerance are satisfactorily screened from among strains grown by the traditional mating method. It is needless to say that the intended strains may be created by a mutation process. As the mutation process, routine methods can be adopted widely, including physical processes with γ ray, ultraviolet ray and temperature difference, etc. and processes with mutagens such as ethldium bromide, nitrogen mustard, diepoxybutane, colchicine, peroxide, and purine derivatives.

One of the new yeast strains was designated *Saccharomyces cerevisiae* P-731 and deposited under FERM BP-7035 at National Institute of Bioscience and Human-Technology Agency of Industrial Science and Technology. The bacteriological properties are described below.

Bacteriological Properties of the Strain P-731
1. Growth state
   Good growth in YM liquid culture medium.
   Cell morphology: spherical to egg shape; 3 to 7×4 to 8 μ.
   MM agar culture medium: good growth; colony (white, glossy, and smooth).
2. Ascospore
   Formed in potassium acetate culture medium; ascospore of spherical shape.
3. Individual physiological properties
   3-1. Optimum growth conditions: temperature of 28 to 32° C.; pH 4.5 to 6.5.
   3-2. Growth range: temperature of 5 to 40° C.; pH 2.5 to 8.0.
   3-3. Assimilation of nitrate salt: none.
   3-4. Fat decomposition: none.
   3-5. Carotenoid generation: none.
   3-6. Prominent organic acid generation: none.
   3-7. Vitamin requirement: biotin and pantothenic acid.
   3-8. Freezing tolerance/sugar tolerance: after thawing of the frozen dough containing 40 parts by weight of sucrose per 100 parts by weight of flour (under 4-week storage), the strain generates $CO_2$ 100 ml or more per 40 g of the dough containing 0.4 g yeast on a dry weight basis at 30° C. for 2 hours.
4. Fermentability and assimilability of carbon source

|  | Fermentability | Assimilability |
|---|---|---|
| D-Glucose | + | + |
| D-Galactose | + | + |
| Maltose | + | + |
| Sucrose | + | + |

The above-mentioned two yeast strains deposited are considered to belong to *Saccharomyces cerevisiae*; the strains have the bacteriological properties described above, but the strains have high fermentation potencies in the super-high sugar range and also in the low to medium sugar range. Such strains have never been found among conventionally known yeast strains. Hence, the two yeast strains are designated new strains. Furthermore, not only the above two new strains are encompassed within the scope of the invention; but also all yeast strains having the properties described above, including artificially created strains and strains from the natural origin, are encompassed within the scope of the invention.

(1) The inventive yeast strains with high leavening abilities in the super-high sugar range may be selected and grown in the manner described below. Those with high sugar tolerance can be obtained, by separating each yeast strain generating $CO_2$ in the amount of 110 ml or more at 30° C. for 2 hours, per 40 g of dough containing 0.4 g of said each yeast strain on a dry weight basis containing sucrose of 40 parts by weight per 100 parts by weight of flour. The inventive strains are sometimes referred to as "US yeast".

(2) The inventive yeast strains with a high leavening ability in the super-high sugar range and freezing tolerance may be selected and grown in the manner described below. After the thawing of frozen dough containing 40 parts by weight of sucrose to 100 parts by weight of flour, each yeast strain generating $CO_2$ in the amount of 100 ml or more at 30° C. for 2 hours per 40 g of the frozen dough containing 0.4 g of said each yeast strain on a dry weight basis is satisfactorily separated. The inventive strains are hereinafter sometimes referred to as "FD-2 yeast".

In accordance with the invention, occasionally, the aforementioned two yeast strains (1) and (2) are collectively called sugar super-tolerant yeast strain.

Owing to the excellent sugar tolerance capable of overthrowing the state of art, the sugar super-tolerant yeast can be used widely for the production of bread items with no sugar to bread items in a low sugar range, like French bread and white bread, as well as confectionery bread and fermented confectioneries prepared from dough at super-high sugar contents, as well as for the production of various bread items using fat or fatty oil or egg or the like. The sugar super-tolerant yeast can be used, for example, for producing coffee cake (bread suitable with coffee, which is preferred by many Americans), bean-jam sweet roll, fruit bread, pastry, butter rolls and croissants.

The process of producing bread using the yeast of the yeast of the present invention is satisfactorily any scratch process (straight dough method and sponge dough method) in a conventional manner and is applicable to frozen bread dough in addition to general bread dough. Examples of the invention are described below.

EXAMPLE 1

The inventive sugar super-tolerant yeast strain (FERM BP-7034) was cultured under the following conditions, using a 30-liter jar fermenter, to produce much thereof.

Seed Culture

Sucrose content (on a glucose basis) 1035 g

Urea 103 g

Monosodium phosphate•dihydrate 20.7 g

Quantity of seed yeast (wet basis) 20 g *1

30-Liter Jar Culture

Sucrose content (on a glucose basis) 1400 g

Urea 140 g

Monosodium phosphate•dihydrate 28 g

Quantity of seed yeast (wet basis) 420 g *2

Maker: Oriental Bio-Service Co., Ltd.

Name: Fermenter CONTROL SYSTEM MC-10

Volume: 30 liters

Agitation: 600 rpm

Aeration volume: 16 liters/min

*1 One platinum loop of the seed was inoculated in a 250-ml YPD culture medium/1-liter Sakaguchi's flask for 2-day culture at 30° C.; the total volume in the 4 flasks of themselves was used as seed yeast.

*2 The cell obtained by the seed culture were separated by centrifugation and rinsed in deionized water; and a part thereof was used.

EXAMPLE 2

According to the assay method of the gas generated by yeast, as defined by Japan Yeast Industry Association, the sugar tolerance of each yeast was assayed. By using the inventive yeast (sugar super-tolerant yeast) FERM BP-7034 and a commercially available regular yeast (product manufactured by Oriental Yeast Co., Ltd.), more specifically, the gas generated from the following blends at 30° C. for 120 minutes was assayed under the following conditions by Fermograph. The results are shown in Table 2.

TABLE 1

(Formula ratio per flour part by weight)

| Formula | 0 | 5 | 10 | 15 | 20 |
|---|---|---|---|---|---|
| Flour | 100 | 100 | 100 | 100 | 100 |
| Sucrose | 0 | 5 | 10 | 15 | 20 |
| Sodium chloride | 0.5 | 0.5 | 0.5 | 0.5 | 0.5 |
| Yeast | 6 | 6 | 6 | 6 | 6 |
| Water | 68 | 65 | 62 | 60 | 58 |

| Formula | 25 | 30 | 35 | 40 | 45 |
|---|---|---|---|---|---|
| Flour | 100 | 100 | 100 | 100 | 100 |
| Sucrose | 25 | 30 | 35 | 40 | 45 |
| Sodium chloride | 0.5 | 0.5 | 0.5 | 0.5 | 0.5 |
| Yeast | 6 | 6 | 6 | 6 | 6 |
| Water | 56 | 54 | 52 | 50 | 48 |

| Formula | 50 |
|---|---|
| Flour | 100 |
| Sucrose | 50 |
| Sodium chloride | 0.5 |
| Yeast | 6 |
| Water | 46 |

Process Conditions

Mixer: Hobart mixer

Mixing: low speed for 3 minutes

Kneading temperature: 30° C.

Fermentation temperature: 30° C.

Assay: total gas volume from dough weight of 40 g at 30° C. for 2 hours assayed by Fermograph (manufactured by Atto Co., Ltd.).

TABLE 2

Comparison of leavening abilities
(unit: ml/40 g · dough/2hr)

| Sucrose content | Inventive US yeast | Regular yeast |
|---|---|---|
| 0 | 219 | 220 |
| 5 | 301 | 303 |
| 10 | 330 | 328 |
| 15 | 325 | 325 |
| 20 | 301 | 295 |
| 25 | 275 | 235 |
| 30 | 235 | 171 |
| 35 | 175 | 114 |
| 40 | 134 | 75 |
| 45 | 80 | 38 |
| 50 | 45 | 18 |

The quantity of yeast contained in 40 g of the dough corresponds to 0.40 g on a dry weight basis.

As apparently shown in the results of Table 2, it was confirmed that the sugar super-tolerant yeast of the invention still retained sugar tolerance (osmotic pressure tolerance) capable of sufficiently fermenting dough at a very high sugar concentration, such as dough containing sucrose in an amount of 30 to 50% to flour.

EXAMPLE 3

Using the inventive US yeast (FERM BP-7034), mini-type bean-Jam sweet roll was prepared from the following blend, by the following process; Table 3 and 4.

TABLE 3

(Formula ratio per flour part by weight)

| Formula | Sponge | | Dough mixing | |
|---|---|---|---|---|
| Flour | 70.0 | | 30.0 | |
| "US yeast" | 4.0 | | 1.0 | |
| "Saka-rich" | 15.0 | | | |
| Dough improve | 0.5 | | 0.2 | |
| Sugar | (Glucose) | 5.0 | (Sucrose) | 5.0 |
| Shortening | | | 10.0 | |
| Skim milk powder | | | 3.0 | |
| Sucrose | | | 40.0 | |
| Sodium chloride | | | 0.35 | |
| Whole egg | 10.0 | | | |
| Water | 19.0 | | | |

TABLE 4

| Process conditions | Sponge | Dough mixing |
|---|---|---|
| Mixing time (minutes) | L2M2 | L2M3↓M3H1 |
| Dough temperature | 26° C. | 28° C. |
| Fermentation (floor) | 2 hours | 90 minutes |
| Fermentation Conditions | 28° C. | 28° C. |
| Dividing weight | | 15 g |
| Bench time | | 15 minutes |

TABLE 4-continued

| Process conditions | Sponge | Dough mixing |
|---|---|---|
| Bean-jam weight (per dough) | | 10 g |
| Final proof condition | | 35° C. · 85% RH about 70 minutes |
| Baking conditions | | 200° C. for 8 minutes |

EXAMPLE 4

Using the inventive US yeast, roll with sucrose was prepared from the following blend at the following conditions; Table 5 and 6. At a sucrose content of 15 to 25 parts by weight, the US yeast was effective, advantageously.

TABLE 5

(Formula ratio per flour part by weight)

| | Formula | | | |
|---|---|---|---|---|
| | Sponge | | Dough mixing | |
| Flour | | 70.0 | | 30.0 |
| "US yeast" | | 3.0 | | |
| Dough improve | | 0.1 | | |
| Sugar | (Glucose) | 3.0 | (Sucrose) | 20.0 |
| Shortening | | | | 10.0 |
| Skim milk powder | | | | 3.0 |
| Sodium chloride | | | | 1.0 |
| Whole egg | | 10.0 | | |
| Water | | 34.0 | | 20.0 |

TABLE 6

Process conditions

| | Sponge | Dough mixing |
|---|---|---|
| Mixing time (minutes) | L2M2 | L2M2↓M3H1 |
| Dough temperature | 26° C. | 28° C. |
| Fermentation (floor) | 2 hours | 50 minutes |
| Fermentation Conditions | 28° C. | 28° C. |
| Dividing weight | | 60 g |
| Bench time | | 15 minutes |
| Final proof condition | | 35° C. · 85% RH about 60 minutes |
| Baking conditions | | 200° C. · 9 minutes |

EXAMPLE 5

Using the inventive US yeast, fruit bread was prepared from the following blend at the following conditions; Table 7 and 8. The resulting product was a confectionery-like bread item having a high content of fruit used therein and with fluffy texture; owing to the combined used of the fermentation flavor liquid "Budou Dane #2" (product of Oriental Yeast Co., Ltd.), the resulting bread was very flavorful and delicious.

TABLE 7

(Formula ratio per flour part by weight)

| | Formula | | | |
|---|---|---|---|---|
| | Sponge | | Dough mixing | |
| Flour | | 70.0 | | 30.0 |
| "US yeast" | | 3.0 | | |
| "Budou Dane #2" | | 5.0 | | |
| Dough improve | | 0.1 | | |
| Sugar | (Glucose) | 3.0 | (Sucrose) | 20.0 |
| Fats and fatty oils (shortening) | | | | 10.0 |
| Sodium chloride | | | | 1.5 |
| Whole egg | | 10.0 | | |
| Skim milk powder | | | | 3.0 |
| Raisin | | | | 70.0 |
| Water | | 30.0 | | 14.0 |

TABLE 8

Process conditions

| | Sponge | Dough mixing |
|---|---|---|
| Mixing time (minutes) | L2M2 | L2M3↓M3H1↓L3 |
| Dough temperature | 26° C. | 28° C. |
| Fermentation (floor) | 2 hours | 60 minutes |
| Fermentation Conditions | 28° C. | 28° C. |
| Dividing weight | | 60 g |
| Bench time | | 15 minutes |
| Molding | | |
| Final proof condition | | 35° C. · 85% RH about 60 minutes |
| Baking conditions | | 200° C. · 10 minutes |

EXAMPLE 6

Using the inventive US yeast, a fermented confectionery (cookie) was prepared from the following blend at the following conditions; Table 9. The resulting product was very sweet with fluffy touch on teeth.

TABLE 9

(Formula ratio per flour part by weight)

| | Formula |
|---|---|
| Flour | 100.0 |
| "US yeast" | 5.0 |
| Sucrose | 40.0 |
| Margarine | 40.0 |
| Whole egg | 10.0 |
| Condensed milk | 0.5 |
| Vanilla oil | 0.3 |
| Water | 10.0 |
| Sodium chloride | 0.5 |

Process Conditions

1. Mix sucrose, margarine, condensed milk and sodium chloride with a beater.
2. Add egg in a two-divided manner and emulsify the egg.
3. Add sifted flour, US yeast, and water and mix the resulting mixture together.
4. Gently mix the mixture with hands.
5. Place the dough in a polyethylene bag and elongate flat wise the dough with hands; cool the dough in a refrigerator to a final stiffness easily moldable enough for molding and punch it.
6. Ferment the dough at room temperature for 20 to 30 minutes and bake the dough at 220° C. for about 13 minutes.

EXAMPLE 7

Using the inventive US yeast and a commercially available regular yeast (manufactured by Oriental Yeast Co., Ltd.), a white bread and a sweet roll item were prepared from the following formulas at the following conditions; Table 10 and 11, according to the scratch bakery process. The results are shown in Table 12.

TABLE 10

(Formula ratio per flour part by weight)
Formula

| | Low sugar content (white bread) dough blend | High sugar content (sweet roll) dough blend |
|---|---|---|
| Flour | 100.0 | 100.0 |
| Sucrose | 5.0 | 25.0 |
| Sodium chloride | 2.0 | 0.5 |
| Yeast | 2.0 | 3.0 |
| Shortening | 5.0 | 6.0 |
| Skim milk powder | 0.0 | 2.0 |
| Water | 65.0 | 52.0 |

TABLE 11

Process conditions

| | Low sugar content (white bread) dough blend | High sugar content (sweet roll) dough blend |
|---|---|---|
| Mixing time (minutes) | L2M2↓L2M2H2 | L2M4↓L1M4H |
| Dough temperature | 28° C. | 28° C. |
| Dividing weight | 450 g | 60 g |
| Bench conditions | 30° C. for 15 minutes | 30° C. for 15 minutes |
| Molding | one loaf | molded into sweet roll |
| Baking conditions | 200° C. for 25 minutes | 200° C. for 10 minutes |

TABLE 12

Comparison by scratch process

| Straight process | Inventive US yeast | Regular yeast |
|---|---|---|
| White bread | | |
| First fermentation conditions | 30° C. for 73 minutes | 30° C. for 75 minutes |
| Final proof conditions | 38° C. for 56 minutes | 38° C. for 57 minutes |
| Specific bread volume | 4.38 | 4.32 |
| Bread quality (softness) | soft | ordinary |
| Bread quality (aging) | slow | ordinary |
| Bread quality (texture) | uniform | ordinary |
| Bread flavor | good | good |
| Texture | soft | ordinary |
| Sweet roll | | |
| First fermentation conditions | 76 minutes | 81 minutes |
| Final proof conditions | 38° C. for 55 minutes | 38° C. for 56 minutes |
| Specific bread volume | 5.21 | 5.09 |
| Bread quality (softness) | soft | ordinary |
| Bread quality (aging) | slow | ordinary |
| Bread quality (texture) | uniform | ordinary |
| Bread flavor | good | good |
| Texture | soft | ordinary |

In the same manner, subsequently, a white bread was prepared according to the scratch process (sponge dough method) from the following formula and under the following conditions. The results are shown below in Table 13.

TABLE 13

(Formula ratio per flour part by weight)

| Formula | 70% intermediate seed bakery process (bread loaf) | |
|---|---|---|
| | Sponge | Dough mixing |
| Flour | 70.0 | 30.0 |
| Sucrose | | 5.0 |
| Sodium chloride | | 2.0 |
| Yeast | 2.0 | |
| Dough improver (Ammonium chloride, calcium carbonate) | 0.1 | |
| Water | 38.5 | 25.0 |

TABLE 14

Process conditions

| | Sponge | Dough mixing |
|---|---|---|
| Mixing time (minutes) | L1M2 | L1M6H3 |
| Dough temperature | 24° C. | 28° C. |
| Fermentation conditions | 30° C. 28° C. for 4 hours | 30° C. for 15 minutes |
| Dividing weight | | 450 g |
| Fermentation (floor) | | 15 minutes or 30 minutes |
| Bench time | | 15 minutes |
| Final proof | | 35° C. · 85% RH |
| Baking conditions | | 200° C. for 20 minutes |

TABLE 15

Comparison by the scratch process

| Sponge dough method | Inventive US yeast | Regular yeast |
|---|---|---|
| Sponge leavening volume for 1 hr | 145 ml | 120 ml |
| Dough leavening volume for 1 hr | 315 ml | 300 ml |
| Final proof | 35° C. for 52 minutes | 35° C. for 55 minutes |
| Specific bread volume | 6.0 | 5.8 |
| Bread quality (softness) | soft | ordinary |
| Bread quality (aging) | slow | ordinary |
| Bread quality (texture) | uniform | ordinary |
| Bread flavor | good | good |
| Texture | soft | ordinary |

As apparently shown above in the results of Table 15, it was confirmed that the inventive US yeast had a leavening ability at the same level as that of regular yeast (for example, Regular Yeast manufactured by Oriental Yeast Co., Ltd.) and could produce excellent bread of stable quality and softness and with large volume, from dough blended with sugar in an amount of 5 to 25% to flour (in the low to high sucrose range) for white bread and sweet roll, according to any of the straight bakery method and the sponge dough method.

EXAMPLE 8

The inventive FD-2 yeast (FERM BP-7035) was cultured and prepared on a large scale, using a 30-liter jar fermenter under the following conditions.

Seed Culture
  Sugar content (on a glucose basis) 1035 g
  Urea 103 g
  Monosodium phosphate•dihydrate 20.7 g
  Quantity of seed yeast (wet basis) 20 g *1

30-Liter Jar Culture
  Sugar content (on a glucose basis) 1400 g
  Urea 140 g
  Monosodium phosphate•dihydrate 28 g
  Quantity of seed yeast (wet basis) 420 g *2
  Maker: Oriental Bio-Service Co., Ltd.
  Name: Fermenter CONTROL SYSTEM MC-10
  Volume: 30 liters
  Agitation: 600 rpm
  Aeration volume: 16 liters/min
  *1 One platinum loop of the seed was inoculated in a 250-ml YPD culture medium/1-liter Sakaguchi's flask for 2-day culture at 30° C.; the total volume in the 4 flasks of themselves was used as seed yeast.
  *2 The cells obtained from the seed culture were separated by centrifugation and rinsed in deionized water; and a part thereof was used.

EXAMPLE 9

The freezing tolerance was compared between the inventive yeast (P-731 FERM BP-7035: FD-2 yeast) and a commercially available freezing tolerant yeast (without sugar tolerance) (FD-1 yeast: product of Oriental Yeast Industry, Co., Ltd.) in various blends with sugar.

More specifically, the inventive yeast prepared as described above was added to and mixed and kneaded with bread dough at the following Table 16. After mixing and kneading, the resulting dough was divided into 40-g portions, which were then fermented at 30° C. and molded thereafter; then, the molded portions were frozen and stored for given periods of time at −20° C. As a control, the commercially available freezing tolerant yeast was used, to prepare such frozen dough in the same manner, for storage.

TABLE 16

(Formula ratio per flour part by weight)

|  | 0 | 5 | 10 | 15 | 20 |
|---|---|---|---|---|---|
| Flour | 100 | 100 | 100 | 100 | 100 |
| Sucrose | 0 | 5 | 10 | 15 | 20 |
| Sodium chloride | 0.5 | 0.5 | 0.5 | 0.5 | 0.5 |
| Yeast | 6 | 6 | 6 | 6 | 6 |
| Water | 68 | 65 | 62 | 60 | 58 |

|  | 25 | 30 | 40 | 50 |
|---|---|---|---|---|
| Flour | 100 | 100 | 100 | 100 |
| Sucrose | 25 | 30 | 40 | 50 |
| Sodium chloride | 0.5 | 0.5 | 0.5 | 0.5 |
| Yeast | 6 | 6 | 6 | 6 |
| Water | 56 | 54 | 50 | 46 |

Process Conditions
  Mixer: Hobart mixer
  Mixing: low speed for 3 minutes
  Dough temperature: 24° C.
  Quantity of divided dough portion: 40 g
  Fermentation prior to dough freezing (floor time): 15 minutes (28° C.)
  Dough freezing: −40° C. for 30 minutes
  Storage of frozen dough: −20° C.
  Thawing: 20° C. for 60 minutes
  Assay: total gas volume from dough weight of 40 g at 30° C. for 2 hours was assayed by Fermograph (manufactured by Atto Co., Ltd.).

TABLE 17

Comparison of fermentability

| | | | | (mg/40 g · dough/2 hr) | | |
|---|---|---|---|---|---|---|
| Period of dough storage | Inventive FD-2 yeast | | | Commercially available freezing tolerant yeast | | |
| under freezing | 1 day | 4 weeks | 8 weeks | 1 day | 4 weeks | 8 weeks |
| sucrose 0% | 205 | 185 | 155 | 210 | 192 | 156 |
| content 5% | 262 | 248 | 224 | 265 | 252 | 221 |
| 10% | 292 | 272 | 251 | 288 | 269 | 249 |
| 15% | 280 | 260 | 243 | 279 | 255 | 241 |
| 20% | 258 | 243 | 230 | 256 | 239 | 228 |
| 25% | 237 | 225 | 211 | 231 | 218 | 205 |
| 30% | 204 | 192 | 180 | 195 | 182 | 169 |
| 40% | 118 | 107 | 103 | 85 | 66 | 45 |
| 50% | 47 | 40 | 35 | 28 | 19 | 12 |

As apparently shown in Table 17 in the results, it was confirmed that the inventive freezing tolerance yeast (FD-2 yeast) had freezing tolerant at the same level as that of the commercially available freezing tolerance yeast and still had sugar super-tolerance capable of sufficiently fermenting dough at a high sugar concentration (even dough at a very high sugar concentration, such as dough containing sucrose in an amount of 30 to 50% to flour).

EXAMPLE 10

Using the inventive FD-2 yeast (FERM BP-7035), coffee cake was prepared from the following blend at the following steps of the following bakery process (general bakery process: scratch process, frozen dough method).

Formula Per Flour Part by Weight

| Flour | 100 |
|---|---|
| Yeast (FD-2 yeast) | 8 |
| Dough improver | 2 |

("010" for frozen dough: product manufactured by Oriental Co., Ltd.)

| Sucrose | 40 |
|---|---|
| Margarine | 25 |
| Sodium chloride | 0.8 |
| Skim milk powder | 6 |
| Whole egg | 25 |
| Water | 20 |
| Flour paste (per dough) | 60 |

("Tokachi milk": product manufactured by Oriental Co., Ltd)

Process Condition

| Mixing time | $L_2M_4H_6 \downarrow M_3H_{10}$ |
|---|---|
| Dough temperature | 25° C. |
| Floor time | 40 minutes |
| Retard temperature | 5° C. |
| Retard time | 15 to 20 minutes |
| Roll-in | being folded in four: once |
| Dividing weigh | 70 g |
| Dough freezing | −40° C. for 30 minutes |
| Dough storage under freezing | −20° C. for 6 weeks |

-continued

| | |
|---|---|
| Thawing | 20° C. for 60 minutes |
| Final proof | 70 minutes |
| Final proof conditions | 35° C. · 85% RH |
| Baking conditions | 200° C. for about 12 minutes |

Because of the high content of sugar, coffee cake with a new taste, such as sweet taste and soft touch, like sponge cake was obtained by baking the dough after thawing, which was a brand-new bread product having new flavor and giving new texture.

Furthermore, blend doughs with addition of sucrose at 10 to 25% to flour in the medium to high sugar range were individually prepared (100 g of flour, 10 to 25 g of sucrose, 0.5 g of sodium chloride, 6 g of yeast and 52 ml of water); the doughs were kneaded and divided into 30-g portions on a flour basis, which were preliminarily fermented at 30° C. for 30 minutes; each portion was molded, frozen and stored for 1 to 3 weeks; after thawing, the gas generated at 30° C. for 120 minutes was assayed by Fermograph. Consequently, it was verified that the inventive freezing tolerant/sugar super-tolerant yeast (FD-2 yeast) had freezing tolerance at the same level as that of standard yeast for frozen dough (for example, FD-1 yeast: product of Oriental Yeast Co., Ltd.), to produce high-quality bread even after the yeast was stored in frozen bakery dough for a long term.

EXAMPLE 11

Frozen dough of the following Table 18 prepared by using the inventive FD-2 yeast at the following Table 19 was thawed, to prepare mini-type bean-jam sweet roll. Herein, "Saka-rich" is a fermentation flavor solution like "Sakadane". These are products of Oriental Yeast Industry, Co., Ltd.

TABLE 18

(Formula ratio per flour part by weight)

| Formula | |
|---|---|
| Flour | 100.0 |
| "FD-2 yeast" | 5.0 |
| "Saka-rich" | 15.0 |
| Dough improve | 1.0 |
| Sucrose | 10.0 |
| Shortening | 10.0 |
| Skim milk powder | 3.0 |
| Liquid inverted sugar | 40.0 |
| Sodium chloride | 0.35 |
| Whole egg | 10.0 |
| Water | 19.0 |

TABLE 19

Process conditions

| | |
|---|---|
| Mixing time (minutes) | $L_2M_4M_6\downarrow M_3H_{10}$ |
| Dough temperature | 25° C. |
| Fermentation (floor) | 40 minutes |
| Fermentation temperature | 28° C. |
| Dividing weight | 15 g |
| Bench time | 15 minutes |
| Bean-jam weight (per dough) | 10 g |
| Dough freezing | −40° C. for 30 minutes |
| Dough storage under freezing | −20° C. for 4 weeks |
| Thawing: | 20° C. for 60 minutes |
| Final proof condition | 35° C. · 85% RH |

TABLE 19-continued

Process conditions

| | |
|---|---|
| | about 70 minutes |
| Baking conditions | 200° C. for about 8 minutes |

EXAMPLE 12

Sweet roll using sucrose was prepared, by using the inventive FD-2 yeast from the following Table 20 at the following Table 21. Even at a sucrose content of 15 to 25 parts by weight, the FD-2 yeast was effective.

TABLE 20

(Formula ratio per flour by weight)

| Formula | |
|---|---|
| Flour | 100.0 |
| FD-2 yeast | 3.0 |
| Dough improve | 1.0 |
| Sucrose | 23.0 |
| Fats and fatty oils (shortening) | 10.0 |
| Skim milk powder | 3.0 |
| Sodium chloride | 1.0 |
| Whole egg | 10.0 |
| Water | 54.0 |

TABLE 21

Process conditions

| | |
|---|---|
| Mixing time (minutes) | $L_2M_4M_6\downarrow M_3H_{10}$ |
| Dough temperature | 25° C. |
| Fermentation (floor) | 30 minutes |
| Fermentation temperature | 28° C. |
| Dividing weight | 60 g |
| Bench time | 15 minutes |
| Dough freezing | −40° C. for 30 minutes |
| Dough storage under freezing | −20° C. for 5 weeks |
| Thawing: | 20° C. for 60 minutes |
| Final proof condition | 35° C. · 85% RH |
| | about 60 minutes |
| Baking conditions | 200° C. for about 9 minutes |

EXAMPLE 13

Fruit bread was prepared by using the inventive FD-2 yeast, after thawing the frozen dough of the following Table 22 as prepared at the following Table 23. The resulting product was a confectionery-like bread item at a high content of fruit used therein and with fluffy taste; owing to the combined use of the fermentation flavor liquid "Budou Dane #2" (product of Oriental Yeast Co. Ltd.) the resulting bread was very flavorful and delicious.

TABLE 22

| Formula | |
|---|---|
| Flour | 100.0 |
| FD-2 yeast | 3.0 |
| "Budou Dane #2" | 5.0 |
| Dough improver | 1.0 |
| Sucrose | 25.0 |
| Shortening | 10.0 |
| Sodium chloride | 1.5 |
| Whole egg | 10.0 |
| Skim milk powder | 3.0 |

TABLE 22-continued

| Formula | |
|---|---|
| Raisin | 70.0 |
| Water | 44.0 |

TABLE 23

| Process conditions | |
|---|---|
| Mixing time (minutes) | L₂M₈↓M5H₆↓L₈ |
| Dough temperature | 26° C. |
| Fermentation (floor) | 60 minutes |
| Fermentation temperature | 28° C. |
| Dividing weight | 60 g |
| Bench time | 15 minutes |

| Molding | |
|---|---|
| Dough freezing | −40° for 30 minutes |
| Dough storage under freezing | −20° C. for 6 weeks |
| Thawing: | 29° C. for 60 minutes |
| Final proof condition | 35° C. · 85% RH about 60 minutes |
| Baking conditions | 200° C. for about 10 minutes |

EXAMPLE 14

Using the inventive FD-2 yeast, a fermented confectionery (cookie) was prepared from the frozen dough of the following Table 24 as prepared at the following process. The resulting product was a fermented confectionery, very sweet with fluffy touch on teeth.

TABLE 24

(Formula ratio per flour part by weight)

| Flour | 100.0 |
|---|---|
| FD-2 yeast | 5.0 |
| Sucrose | 40.0 |
| Margarine | 40.0 |
| Whole egg | 10.0 |
| Condensed milk | 0.5 |
| Vanilla oil | 0.3 |
| Water | 10.0 |
| Sodium chloride | 0.5 |

Process Condition
1. Mix refined sucrose, margarine, condensed milk and sodium chloride with a beater.
2. Add egg in a two-divided manner and emulsify the egg.
3. Add sifted flour, FD-2yeast and water and mix the resulting mixture together.
4. Gently knead the mixture with hands.
5. Place the dough in a polyethylene bag and flat wise and the dough with hands; cool the dough in a refrigerator to a final stiffness easily moldable enough for molding and punch it.
6. Ferment the dough at room temperature for 20 to 30 minutes.
7. Freeze the molded dough at −40° C. for 30 minutes.
8. Store the dough at −20° C. for 6 weeks.
9. Thaw the dough at 20° C. for 60 minutes.
10. Bake the dough at 220° C. for about 13 minutes.

EXAMPLE 15

Using the inventive FD-2 yeast and a commercially available regular yeast (manufactured by Oriental Yeast Industry, Co., Ltd.), a white bread and a sweet roll item were prepared from the following Table 25 under the following conditions, according to the scratch bakery process (straight bakery process). The results are shown in Table 27.

TABLE 25

(Formula ratio per flour part by weight)

| Formula | Low sugar content (white bread) | High sugar content (sweet roll) |
|---|---|---|
| Flour | 100 | 100 |
| Sucrose | 5 | 25 |
| Sodium chloride | 2 | 0.5 |
| Yeast | 2 | 3 |
| Shortening | 5 | 6 |
| Skim milk powder | 0 | 2 |
| Water | 65 | 52 |

TABLE 26

| Process conditions | | |
|---|---|---|
| Mixing time (minutes) | L2M2↓L2M2H2 | L2M4↓L1M4H |
| Dough temperature | 28° C. | 28° C. |
| Dividing weight | 450 g | 60 g |
| Bench time | 30° C. for 15 minutes | 30° C. for 15 minutes |
| Molding | one loaf | molded into sweet roll |
| Baking conditions | 200° C. for 25 minutes | 200° C. for 10 minutes |

TABLE 27

Comparison by the scratch bakery process

| Straight process | Inventive FD-2 yeast | Regular yeast |
|---|---|---|
| White bread loaf: first fermentation | 30° C. for 70 minutes | 30° C. for 75 minutes |
| Final proof | 38° C. for 58 minutes | 38° C. for 57 minutes |
| Specific bread volume | 4.42 | 4.32 |
| Bread quality (softness) | soft | ordinary |
| Bread quality (aging) | slow | ordinary |
| Bread quality (texture) | uniform | ordinary |
| Bread flavor | good | good |
| Bread texture | soft | ordinary |
| Sweet roll: first fermentation | 75 minutes | 81 minutes |
| Final proof | 38° C. for 56 minutes | 38° C. for 56 minutes |
| Specific bread volume | 5.30 | 5.09 |
| Bread quality (softness) | soft | ordinary |
| Bread quality (aging) | slow | ordinary |
| Bread quality (texture) | uniform | ordinary |
| Bread flavor | good | good |
| Bread texture | soft | ordinary |

Additionally, it is verified from the aforementioned examples that the freezing tolerant, sugar super-tolerant yeast of the invention has an excellent leavening ability of non-frozen dough, to produce various bakery products. The inventive yeast exerted sufficient freezing tolerance and sugar super-tolerance in frozen dough, to prepare excellent bakery products from the frozen dough, even by the frozen dough process.

EXAMPLE 16

Using the inventive P-731 strain (FERM BP-7035), Danish pastry was prepared from the following Table 28 under the following Table 29 according to the process of refrigerated dough in large portions. The resulting Danish pastry was highly suppressed of acid odor and fermentation smell and was greatly flavorful with butter and tasted very delicious. As described above, it was confirmed that the inventive yeast could be used for the refrigerated dough process.

TABLE 28

Pastry process conditions (Formula ratio per flour per part by weight)

| | |
|---|---:|
| Flour | 100.0 |
| Sucrose | 20.0 |
| Sodium chloride | 1.0 |
| Skim milk powder | 3.0 |
| Margarine | 20.0 |
| Whole egg | 20.0 |
| Dough improver | 0.5 |
| Yeast | 6.0 |
| Water | 40.0 |
| Roll-in fats and fatty oils | 50.0 |

TABLE 29

| Process conditions | |
|---|---|
| Mixing time (minutes) | $L_2M_3 \downarrow L_1M_3H_1$ |
| Dough temperature | 25° C. |
| Fermentation (floor) | 60 minutes |
| Retard | |
| Dough weight in large portions | 2 kg |
| Storage temperature (° C.) | 5° C. for 12 hours |
| Roll-in | Being folded in tree : thrice |
| Molding | square type |
| Final proof condition | 35° C. · 75% RH |
| | 75 minutes |
| Baking conditions | 210° C. for about 12 minutes |

Advantages of the Invention

In accordance with the invention, yeasts have been developed, having leavening abilities and high sugar tolerance in the ultra-high sugar range, and yeasts with a high leavening ability in the super-high sugar range and freezing tolerance in the ultra-high sugar range.

The inventive sugar super-tolerant yeasts are applicable widely to the production of from confectionery bread to fermented confectionery from dough formula of ultra-high sugar content, in addition to bread in the low sugar range, and are additionally applicable to various bread items using fat or fatty oil or eggs, and are widely applicable to frozen dough process as well as general bakery process. For example, the inventive yeasts can be used for producing coffee cake (bread suitable for coffee, which is popular among many Americans), sweet roll, fruit bread, pastry, butter roll, croissant and the like.

What is claimed is:

1. A biologically pure culture of *Saccharomyces cerevisiae* yeast which has a sugar tolerance such that the yeast is capable of generating at least 100 ml of $CO_2$ per 40 grams of dough containing 0.4 g of the yeast on a dry basis upon fermentation at 30° C. for two hours, wherein said 40 grams of dough has the following formula: 100 parts by weight of flour, 40 parts by weight of sucrose, 0.5 parts by weight of sodium chloride, 6 parts by weight of yeast as wet yeast and 50 parts by weight water.

2. A biologically pure culture of *Saccharomyces cerevisiae* yeast which has a sugar tolerance such that the yeast is capable of generating at least 100 ml of $CO_2$ per 40 grams of dough containing 0.4 g of the yeast on a dry basis upon fermentation at 30° C. for two hours, after a. mixing 100 parts by weight of flour, 40 parts by weight of sucrose, 0.5 part by weight of sodium chloride, 6 parts by weight of the yeast as wet yeast, and 50 parts by weight of water to form a dough;

b. fermenting the dough formed in step (a) at 28° C. for 15 minutes;

c. freezing the dough fermented in step (b) at −40° C. for 30 minutes;

d. storing the frozen dough at −20° C. for four weeks; and then e. thawing the stored dough at 20° C. for 60 minutes.

3. A biologically pure culture of *Saccharomyces cerevisiae* P-731, FERM BP-7035.

4. A method for obtaining yeast capable of generating at least 110 ml of $CO_2$ per 40 grams of dough containing 0.4 g of the yeast on a dry weight basis after fermenting at 30° C. for two hours, comprising:

a. mixing 100 parts by weight of flour, 40 parts by weight of sucrose, 0.5 part by weight of sodium chloride, 6 parts by weight of the yeast as wet yeast, and 50 parts by weight of water to form a dough;

b. forming portions of the dough into 40 gram portions;

c. fermenting the dough portions formed in step (b) at 30° C. for two hours and assaying the amount of $CO_2$ generated; and d. screening and recovering the yeast which is capable of generating at least 110 ml of $CO_2$ per 40 grams of dough.

5. A method for obtaining yeast capable of generating at least 100 ml of $CO_2$ per 40 grams of dough containing 0.4 g of the yeast on a dry weight basis after fermenting at 30° C. for two hours, comprising:

a. mixing 100 parts by weight of flour, 40 parts by weight of sucrose, 0.5 part by weight of sodium chloride, 6 parts by weight of the yeast as wet yeast, and 50 parts by weight of water to form a dough;

b. forming portions of the dough into 40 gram portions;

c. fermenting the dough portions formed in step (b) at 28° C. for 15 minutes;

d. freezing the portions fermented in step (c) at −40° C. for 30 minutes;

e. storing the frozen portions at −20° C. for four weeks;

f. thawing the stored portions at 20° C. for 60 minutes;

g. fermenting the thawed portions at 30° C. for two hours to assay the amount of $CO_2$ generated; and h. screening and recovering the yeast capable of generating 110 ml or more $CO_2$ per 40 grams of dough.

* * * * *